US009823169B1

(12) United States Patent
Witt, III et al.

(10) Patent No.: US 9,823,169 B1
(45) Date of Patent: Nov. 21, 2017

(54) CYCLONIC FUGITIVE DUST SAMPLER

(71) Applicants: Emitt C. Witt, III, Rolla, MO (US); David J. Wronkiewicz, Rolla, MO (US)

(72) Inventors: Emitt C. Witt, III, Rolla, MO (US); David J. Wronkiewicz, Rolla, MO (US)

(73) Assignee: The United States of America as Represented by the Secretary of the Department of the Interior, Washington, DC (US)

( * ) Notice: Subject to any disclaimer, the term of this patent is extended or adjusted under 35 U.S.C. 154(b) by 515 days.

(21) Appl. No.: 14/257,092

(22) Filed: Apr. 21, 2014

Related U.S. Application Data

(60) Provisional application No. 61/814,704, filed on Apr. 22, 2013.

(51) Int. Cl.
*G01N 1/04* (2006.01)
*B04C 9/00* (2006.01)

(52) U.S. Cl.
CPC .......... *G01N 1/04* (2013.01); *B04C 2009/002* (2013.01); *B04C 2009/008* (2013.01)

(58) Field of Classification Search
CPC .. G01N 1/04; G01N 1/2211; G01N 2001/028; G01N 1/02; G01N 1/24; G01N 2015/0288; G01N 2015/149; E01H 1/00; E01H 1/108; E01H 5/062
USPC ....................................... 73/863, 21, 863.22
See application file for complete search history.

(56) References Cited

U.S. PATENT DOCUMENTS

| | | | |
|---|---|---|---|
| 5,519,420 A | 5/1996 | Zorn et al. | |
| 6,058,557 A | 5/2000 | Berndt | |
| 6,195,837 B1 * | 3/2001 | Vanderlinden | E01H 1/042 15/340.3 |
| 6,383,301 B1 * | 5/2002 | Bell | B01J 8/0015 118/716 |
| 6,444,003 B1 * | 9/2002 | Sutcliffe | B01D 46/2403 15/340.4 |

(Continued)

OTHER PUBLICATIONS

U.S. Environmental Protection Agency. 1980. 435 atmospheric sampling: U.S. Environmental Protection Agency, Air Pollution Training Institute, course manual, lesson 9 (pp. 168-179). http://nepis.epa.gov/EPA/html/DLwait.htm?url=/Exe/ZyPDF.cgi/9100ZFOU.PDF?Dockey=9100ZFOU.Pdf (accessed Apr. 17, 2014).

*Primary Examiner* — Hezron E. Williams
*Assistant Examiner* — Marrit Eyassu
(74) *Attorney, Agent, or Firm* — James Mitchell

(57) ABSTRACT

A dust sampling system including a dust sampler and a vehicle on which the dust sampler is placed. The dust sampler has a suction unit, a cyclone, a dust collection container, and an air intake conduit. The suction unit draws in air containing dust particles. The cyclone centrifugally separates the dust particles from the drawn-in air. The cyclone has an air input port, a particle discharge end, and an air output port connected to the suction unit. A dust collection container is positioned underneath the cyclone to receive the separated dust particles from the cyclone. The air intake conduit has an air inlet and an air outlet connected to the air input port of the cyclone. The suction unit draws in the air containing the dust particles into the air inlet of the air intake conduit while the vehicle moves to collect samples of fugitive dust from a road.

17 Claims, 8 Drawing Sheets

(56) References Cited

U.S. PATENT DOCUMENTS

| | | | |
|---|---|---|---|
| 7,074,261 B2* | 7/2006 | Murphy | B01D 45/16 55/324 |
| 7,128,770 B2 | 10/2006 | Oh et al. | |
| 2004/0055470 A1* | 3/2004 | Strauser | E01H 1/0827 96/417 |
| 2005/0158172 A1* | 7/2005 | Snyder | F01D 15/10 415/206 |
| 2006/0254226 A1* | 11/2006 | Jeon | A47L 9/1625 55/345 |
| 2009/0113856 A1 | 5/2009 | Cooper et al. | |
| 2009/0202311 A1 | 8/2009 | Deal et al. | |
| 2010/0095559 A1* | 4/2010 | Buckner | E02F 3/8825 37/304 |
| 2013/0026267 A1* | 1/2013 | Roh | B02C 17/04 241/37.5 |
| 2013/0104335 A1* | 5/2013 | Conrad | A47L 5/24 15/327.2 |
| 2014/0017018 A1* | 1/2014 | Blais | E01H 1/0836 406/39 |
| 2014/0255133 A1* | 9/2014 | Wilkinson | B04C 5/185 414/291 |

* cited by examiner

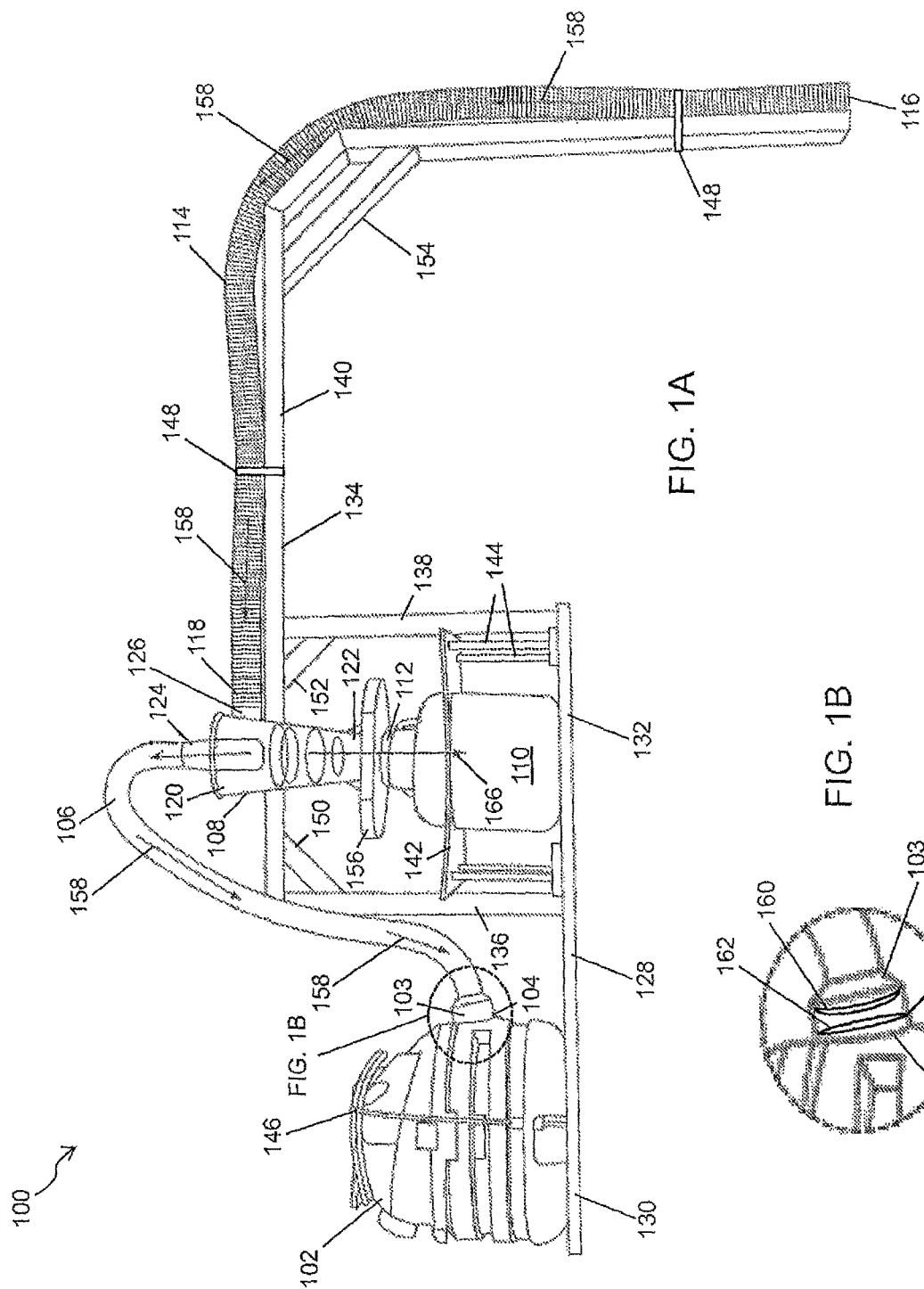
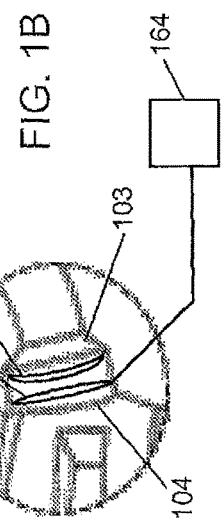
FIG. 1A
FIG. 1B

| Sample Designation | Trace Element (mg/kg) | | | | | | | Sample Quantity (g) | Intake Height (cm) |
|---|---|---|---|---|---|---|---|---|---|
| | Pb | Zn | Co | Ni | Cu | Cd | As | | |
| C-1 | 14.4 | 23.2 | 3.1 | 7.2 | 4.7 | 0.2 | 10.7 | 3 | 50.8 |
| C-2 | 14.2 | 24.8 | 3.4 | 7.8 | 4.7 | 0.3 | 12.6 | 6 | 50.8 |
| C-3 | 11.1 | 22.8 | 2.9 | 7.4 | 3.5 | 0.2 | 11.7 | 6 | 50.8 |
| C-5 | 10.8 | 23.9 | 3.0 | 7.6 | 3.8 | 0.2 | 11.7 | 11 | 50.8 |
| C-7 | 11.4 | 25.2 | 3.0 | 7.4 | 4.7 | 0.2 | 10.2 | 4 | 88.9 |
| C-8 | 11.9 | 25.4 | 3.1 | 7.7 | 4.3 | 0.2 | 11.8 | 3 | 88.9 |
| C-9 | 8.5 | 21.7 | 2.5 | 8.0 | 3.2 | 0.2 | 17.4 | 2 | 88.9 |
| Mean (C1-C9) | 11.8 | 23.9 | 3.0 | 7.59 | 4.13 | 0.21 | 12.3 | -- | -- |
| Standard Deviation (C1-C9) | 2.04 | 1.37 | 0.27 | 0.27 | 0.63 | 0.04 | 2.38 | -- | -- |
| DU1 | 4588 | 433 | 13.4 | 21.9 | 284 | 6.3 | 135 | 27 | 50.8 |
| DU2 | 58.5 | 31.0 | 4.2 | 4.7 | 11.7 | 0.4 | 5.6 | 13 | 50.8 |
| Digestion Vessel Blank | 0.025 | <.02† | <.02† | <.02† | <0.02† | <.02† | <0.02† | -- | -- |
| SRM 2711-1 | 1419 | 354 | 7.9 | 17.7 | 122 | 51.9 | 116 | -- | -- |
| SRM 2711-2 | 1431 | 358 | 7.9 | 17.7 | 125 | 52.9 | 116 | -- | -- |
| SRM 2711-3 | 1422 | 358 | 7.9 | 17.7 | 125 | 53.3 | 117 | -- | -- |
| SRM 2587-1 | 3367 | 304 | 8.0 | 22.2 | 146 | 2.0 | 17.4 | -- | -- |
| SRM 2587-2 | 3491 | 317 | 8.6 | 23.7 | 153 | 2.3 | 17.9 | -- | -- |
| SRM 2587-3 | 3399 | 316 | 8.2 | 21.9 | 161 | 2.0 | 17.0 | -- | -- |

†Less than method determination level.

FIG. 8

CYCLONIC FUGITIVE DUST SAMPLER

CROSS-REFERENCE TO RELATED APPLICATION(S)

This application is related to and claims the benefit of priority to U.S. Provisional Application Ser. No. 61/814,704 filed Apr. 22, 2013 in the U.S. Patent and Trademark Office, the contents of which are incorporated herein by reference.

STATEMENT OF GOVERNMENT INTEREST

The invention described herein may be manufactured, used, and licensed by or for the U.S. Government for governmental purposes without payment of any royalties thereon.

BACKGROUND

The present invention relates in general to the collection of samples of fugitive dust.

Fugitive dust is an airborne contaminant that is common in rural areas where unsurfaced gravel and dirt are the predominant road surfaces and in urban areas close to heavy industry and truck traffic, thus generating higher population exposures and accompanying public health impacts. The health effects of fugitive dust range from aggravation of the respiratory system to systemic addition of trace elements in the blood through inhalation and ingestion. Studies have shown that lead (Pb) in dust is responsible for significant increases in blood-Pb levels of persons living in close proximity to Pb-dust sources such as mining, smelting, recycling, and other industrial activities (Murgueytio et al., 1998; Kerin and Lin, 2010; Johnson and Bretsch, 2002; Thornton et al., 1990; Needleman et al., 1990). Trace metals associated with fly ash and bottom ash released from power plants and incorporating onto road surfaces can also have a direct effect on human health (Zeneli et al., 2011). Contaminated unsurfaced roads can be a persistent and unavoidable health hazard for those living beside or regularly traveling these roads.

A thorough characterization of fugitive dust generated from road surfaces in areas that have been shown to have trace metal and other contamination from legacy industrial processes is largely unknown. The collection of samples for the chemical characterization of fugitive dust has been largely limited to point sources where swabs are obtained from homes, vehicles, roadside vegetation, deposits on soils, cascading impactors, or collected by installing open pans near unsurfaced roadways in potentially contaminated areas (Erel and Torrent, 2010; Duggan and Inskip, 1985; Kerin and Lin, 2010).

These methods do not support repeatability and representativeness (Que Hee et al., 1985). Point-collections limit data interpretation to a small area or require the investigator to make gross assumptions about the origin of the sample collected. Swabs from homes and dashboards of vehicles only represent those particular locations, and contaminated dust collected in these environments is difficult to track back to a road surface. Roadside vegetation only represents a single point along a roadway, and many samples would need to be collected to represent an 8- to 16-km reach. Pan collection is generally unattended and can be compromised by vandals or weather and roadside vegetation; several of these would need to be deployed to represent an entire road reach. Surface soils that are alleged to be "transported dust" do not provide defensible results because the sample can be a mixture from several sources. Impactors are focused on particle size delineation collecting size ranges that will be harmful when inhaled and do not take into consideration that particle ingestion of all suspended sizes is a much larger contributor to elevated blood-Pb levels (Steele et al., 1990; Biggins and Harrison, 1980; Barltrop and Meek, 1979). Also, these samplers use greases, oils, and other compounds that facilitate collection of samples for analysis. This has been recognized as a problem for representative chemical analysis (USEPA, 1983).

Furthermore, and most importantly, these methods neither produce the needed quantity of sample for rigorous geochemical characterization and reference that would include the need for several grams of material to perform X-ray diffraction, total and sequential extraction, particle size analysis, gravity separation, and repeat analysis, nor provide a spatially integrated characterization of the health hazard. Given the human health concern of fugitive dust, field methods need to be refined to provide a representative, repeatable, and sufficient quantity of sample to better characterize the chemical hazard of this exposure mechanism.

SUMMARY

To achieve a "better sampling" for fugitive road dust studies, a cyclonic fugitive dust (CFD) sampler is provided that centrifugally separates dust from drawn-in air and collects the dust from a moving vehicle over a reach of roadway (e.g., 8- to 16-km). More specifically, the CFD sampler collects fugitive dusts generated by a moving vehicle for the purpose of collecting a large amount of sample to facilitate extensive chemical, physical, and microscopic characterization and reference (e.g., chemical digestion, scanning electron microscope (SEM), X-ray diffraction, and other analyses).

The sampler is capable of collecting large quantities of fugitive dust directly from suspension at the time of generation from the moving vehicle before it interacts with other substrates in the immediate environment and without gross assumptions regarding its origin. The sampler allows for the collection of sufficient sample to characterize the health hazards associated with living along and traveling on surfaced, and specifically unsurfaced, roadways, and provides a mechanism for providing a standardized, repeatable collection methodology for chemical characterization that can support regulatory monitoring to protect human health. It also provides the ability to make intake height adjustments for collection from the moving vehicle at various heights, and also can use GPS technology to track exact locations of sampling reaches.

In accordance with an embodiment of the invention, there is provided a dust collection system having a dust sampler and a vehicle on which the dust sampler is placed. The dust sampler has a suction unit, a cyclone, a dust collection container, and an air intake conduit. The suction unit draws in air containing dust particles. The cyclone centrifugally separates the dust particles from the drawn-in air. The cyclone has an air input port, a particle discharge end, and an air output port connected to the suction unit. A dust collection container is positioned underneath the cyclone to receive the separated dust particles from the cyclone. The air intake conduit has an air inlet and an air outlet connected to the air input port of the cyclone. The suction unit draws in the air containing the dust particles into the air inlet of the air intake conduit while the vehicle moves to collect samples of fugitive dust from a road.

In accordance with another embodiment of the invention, there is provided a cyclonic dust collector having a suction unit, a cyclone, a dust collection container, and an air intake conduit. The suction unit draws in air containing dust particles. The cyclone centrifugally separates the dust particles from the drawn-in air. The cyclone has an air input port, a particle discharge end, and an air output port connected to the suction unit. The dust collection container is positioned underneath the cyclone to receive the separated dust particles from the cyclone. The air intake conduit has an air inlet and an air outlet connected to the air input port of the cyclone. A height of the air inlet above a surface to be sampled is adjustable.

In accordance with another embodiment of the invention, there is provided a method of collecting samples of fugitive dust, including providing a dust sampler having a suction unit, a cyclone, a dust collection container, and an air intake conduit. The suction unit draws in air containing dust particles. The cyclone centrifugally separates the dust particles from the drawn-in air. The cyclone has an air input port, a particle discharge end, and an air output port connected to the suction unit. The dust collection container is positioned underneath the cyclone to receive the separated dust particles from the cyclone. The air intake conduit has an air inlet and an air outlet connected to the air input port of the cyclone. The dust sampler is placed on a vehicle, and a height of the air inlet of the air intake conduit is positioned at a desired height above a road surface. The suction unit is turned on to draw air containing the dust particles into the air inlet of the air intake conduit while the vehicle moves to collect samples of fugitive dust on the road. The vehicle is driven along the road for a predefined distance at a predefined speed while tracking a position of the dust sampler as the vehicle moves using a data logger of a Geospatial Positioning System unit. After the sample has been collected, the dust collection container is removed and stored for subsequent analysis.

BRIEF DESCRIPTION OF THE DRAWINGS

Various aspects and advantages of the invention will become apparent from the following detailed description, taken in conjunction with the accompanying drawings. The drawings are not necessarily drawn to scale. In the drawings:

FIG. 1A is a side view of a cyclonic fugitive dust sampler according to an embodiment of the present invention;

FIG. 1B is a close-up view of an intake adapter of the cyclonic fugitive dust sampler of FIG. 1

FIG. 8 shows results of partial-digestion analysis of particle samples collected by the cyclonic fugitive dust sampler of FIG. 1, digestion blank, standard reference materials digested in triplicate, and test samples from two lead-contaminated roads.

DETAILED DESCRIPTION OF THE PREFERRED EMBODIMENTS

Figure 2:
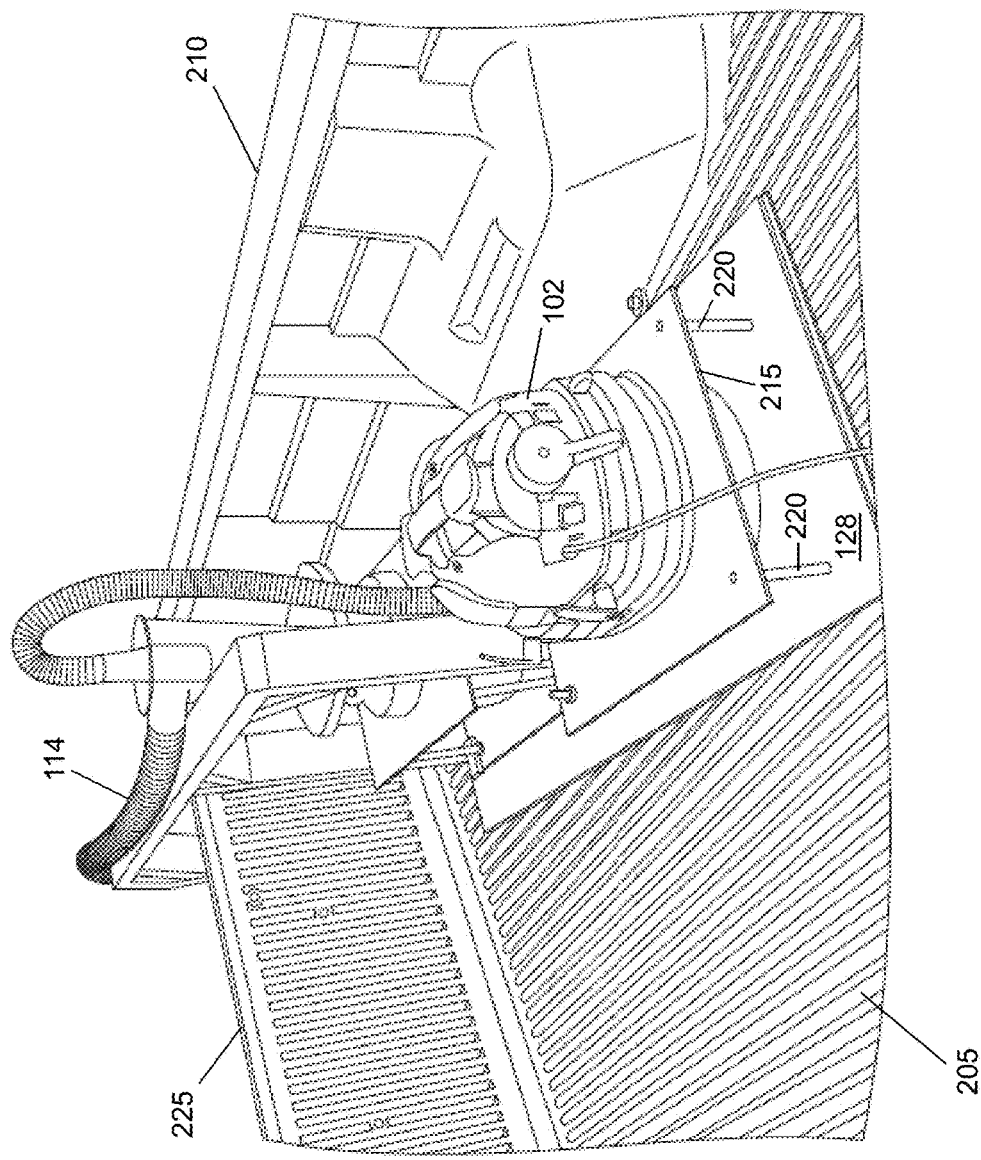
FIG. 2 is a perspective end view of the cyclonic fugitive dust sampler of FIG. 1 placed in a pickup truck bed.

Described herein are a cyclonic fugitive dust (CFD) sampling system, a cyclonic dust sampler, and a method of collecting fugitive dust samples using a moving vehicle that can be used for fugitive dust studies, in particular, where trace metal contamination of these suspended solids is a concern.

FIG. 1A is a side view of a cyclonic fugitive dust sampler 100 according to an embodiment of the invention. The sampler 100 includes a suction unit 102 with an intake adapter 103 connected to an air intake port 104 and a suction hose 106 connected to the intake adapter 103, a cyclone 108, a dust collection container 110 with a cap 112, and an air intake conduit 114 with an air inlet 116 and an air outlet 118. The cyclone 108 has a conical shape with a top end 120 having a larger diameter than a particle discharge or bottom end 122. The cyclone 108 has an output port 124 located at the top end 120 and an input port 126 located near the top end 120. The input port 126 connects to the air intake conduit 114, and the output port 124 connects to the suction hose 106. The bottom end 122 of the cyclone 108 is located above the dust collection container 110.

The sampler 100 is mounted on a frame. In the embodiment of the invention shown in FIG. 1A, the frame includes a base 128 having a first end 130 and a second end 132; a conduit support member 134 having a first leg 136, a second leg 138, and a conduit arm 140; and a container support member 142 with an opening that receives the dust collection container 110 and legs 144 that attach to the base 128. The suction unit 102 is attached to the first end 130 of the base 128, for example, by using plastic wire clamps 146, at a height sufficient to support the suction unit 102. The container support member 142 is attached to the second end 132 of the base 128 between the first leg 136 and the second leg 138 at a height sufficient to support the dust collection container 110. The air intake conduit 114 is secured to the conduit arm 140 using plastic wire clamps 148, for example. Angle brackets 150, 152, 154 provide support for the conduit arm 140. A cap mount 156 has an opening to receive the bottom end 122 of the cyclone 108. An underside of the cap mount 156 has a recess sized to receive the cap 112, which is secured into the recess, for example, by being glued into the recess. The dust collection container 110 is twist screwed onto the cap 112. The cap 112 has a hole in it to allow the dust collection container 110 to receive dust particles from the cyclone 108. Securing the cap 112 to the recessed area provides a secure attachment for the dust collection container 110 and allows for easy replacement of exchangeable dust collection containers 110 between sampling locations. The dust collection container 110 can be easily removed for emptying or replacement by unscrewing it from the cap 112 and lifting it from the container support member 142.

The frame can be constructed of wood, for example, and can be constructed in other configurations suitable to retain the suction unit 102, the dust collection container 110, the cyclone 108, and the air intake conduit 114 in place. In the embodiment shown in FIG. 1A, the suction unit 102 may be a vacuum, such as a 5.5 peak horsepower shop vacuum with an airflow rate of 5.52 m$^3$/min. Arrows 158 show suction air flow direction). The dust collection container 110 is a 10-L high-density polyethylene (HDPE) Nalgene container. The air intake conduit 114 is a clear, flexible polyvinyl chloride (PVC) tubing having an inner diameter of 6.35 cm. The cyclone 108 is a Dust Deputy Cyclone made of high-density polyethylene from Onieda Air Systems. The cap 112 is a number 415 wide-mouth Nalgene cap.

The dust collection container 110 collects particles larger than about 1 μm. A secondary filter 160, such as a 5-μm mesh tortuous-path filter, is attached to the intake adaptor 103 that connects to the air intake port 104 of the suction unit 102 as shown in the close-up view of the intake adapter 103 in FIG. 1B. This effectively traps extremely fine particles, for example, less than about 1 μm-sized particles, that do not deposit in the dust collection container 110.

A static pressure sensor 162 may be added, if desired, to the air intake port 104 of the suction unit 102 before adding the filter 160. The sensor 162 is attached to an analog gauge 164 that measures pressure changes in units of water column and is used to test the airflow changes resulting from filter loading. Alternatively, an air flow meter can be used instead of the static pressure sensor 162.

All parts that come into contact with the sample are either PVC or HDPE, with the exception of the static pressure sensor 162, and are acid washed with 5% nitric acid (HNO$_3$) solution, rinsed with deionized water, and allowed to air dry before deployment.

The sampler 100 presented herein uses a cyclonic dust collection design. The suction unit 102 draws air into the air intake conduit 114. The arrows 166 show suction air flow direction. Cyclonic separation effectively removes particles from a fluid by establishing a helical flow pattern inside a conical container. The vortex generated in the cyclone 108 acts on the entrained particles, creating centrifugal forces that push the particles to the walls of the cyclone 108, allowing them to slow by friction processes and slide down the sides of the cyclone 108 and into the dust collection container 110 as represented by arrow 166. The cyclone 108 in the collection air stream removes the large particle component of the fugitive dust before affecting the filter 160. This prevents filter blockage due to mesh space filling and loss of suction in the sampler 100, promoting greater collection efficiency and longer collection times and enables a larger volume of sample per unit distance of road surface.

Figure 3:
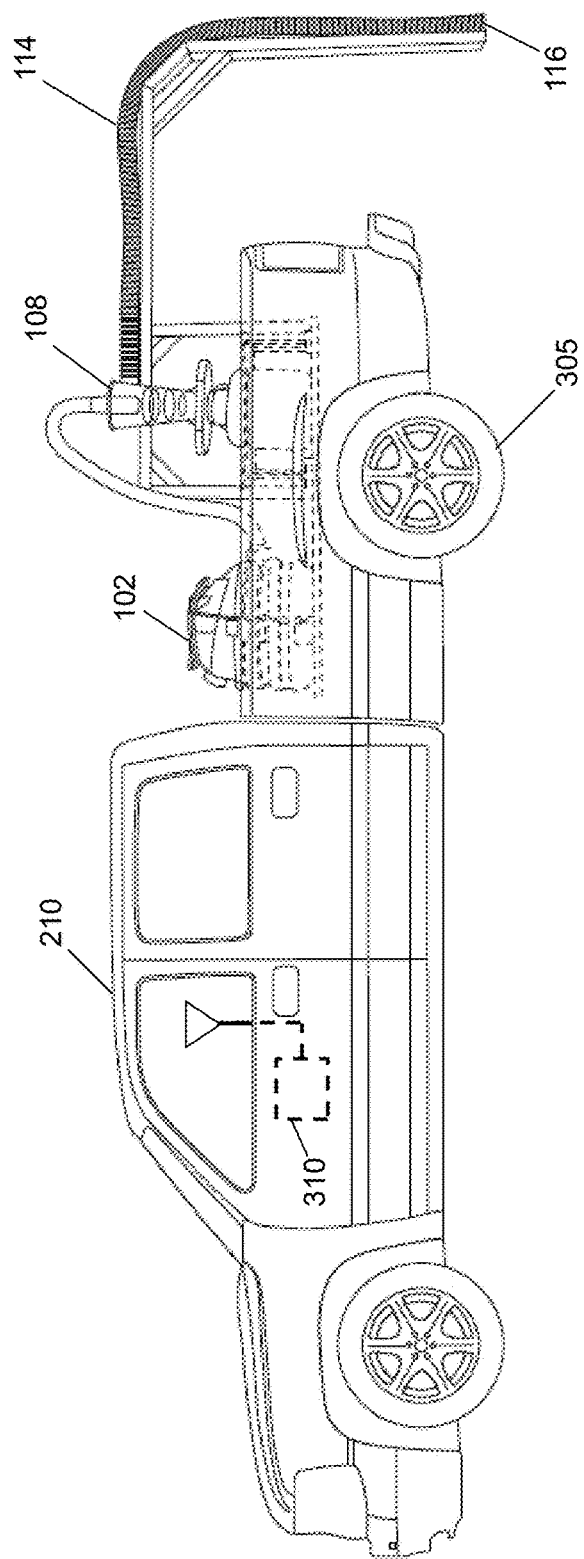
FIG. 3 is a side view of the pickup truck of FIG. 2 with the cyclonic fugitive dust sampler deployed in the truck bed.

In operation, the CFD sampler 100 is deployed, for example, by positioning the sampler 100 in a rear-most area of a bed 205 of a pickup truck 210 as shown in FIGS. 2 and 3. FIG. 2 shows an alternative to mounting the suction unit 102 to the frame base 128. In FIG. 2, the suction unit 102 is placed into an opening in a suction unit support member 215 that has legs 220 that attach to the base 128. The sampler 100 is positioned so that the air intake conduit 114 reaches over an edge or tailgate 225 of the bed 205 behind rear tires 305 and on the opposite side of an exhaust pipe. The optimal distance from a back of the truck 210 to the air inlet 116 is about 90 cm; however, this may vary depending on the make and model of truck. The air inlet 116 is positioned so that it collects suspended dust and not fine sand to granule-sized particles thrown by the vehicle tires 305. This is accomplished by angling the sampler 100 at about 45 degrees from a longitudinal axis of the tailgate 225.

A user can place the air inlet 116 at any height above the road surface by using the plastic wire clamps 148, for example, to hold the air intake conduit 114 to the conduit arm 140. The frame is secured to the vehicle 210 and holds the dust collection container 110, the cyclone 108, and the suction unit 102 in place while the vehicle 210 is moving and samples are being collected. After setting the sampler 100 in the proper position and securing it to prevent movement, the track log setting is selected on a hand-held Geospatial Positioning System (GPS) unit 310, the suction unit 102 is turned on, and the route of unsurfaced road is driven for a user-defined length at a speed of about 40.2 to 56.3 km/hour. The suction unit 102 is powered by a DC/AC inverter mounted inside the vehicle 210. At the conclusion of the sampling event, the dust collection container 110 is weighed, and the sample is transferred from the dust collection container 110 to a certified acid-washed 118 mL storage container and labeled with pertinent information. The dust collection container 110 is weighed before and after sampling in the field using a portable electronic scale with measurement capability to the nearest gram. The secondary filter 160 is removed from the intake adaptor 103 of the suction unit 102 and stored in a labeled polyethylene sampling bag. All field notes are reconciled to the identification information on the sample storage containers, and the containers are placed in a clean dry cooler for transport to the laboratory.

Before collecting another sample, the entire sampler 100 is dismantled for washing and acid-rinsing of the cyclone 108, replacement of the air intake conduit 114, and cleaning of the suction hose 106 and the intake adapter 103. To save time, used tubing may be replaced with precleaned and acid-rinsed tubing of the same specifications. The air intake conduit 114 is made from PVC tubing because the material can be bent around a small radius without collapsing, is clear so obstructions can be identified and removed, and resists repeated acid washing without becoming brittle through degradation. The dust collection container 110 is not cleaned in the field. Additional pre-cleaned and acid-rinsed dust collection containers are exchanged between each sampling site. All sampler components should be dry before sample collection or a substantial amount of sample may be lost to the walls of each component. Under optimal conditions and with careful pre-field planning, about 6 to 10 samples can be collected in a 10-hour day.

Figure 4:
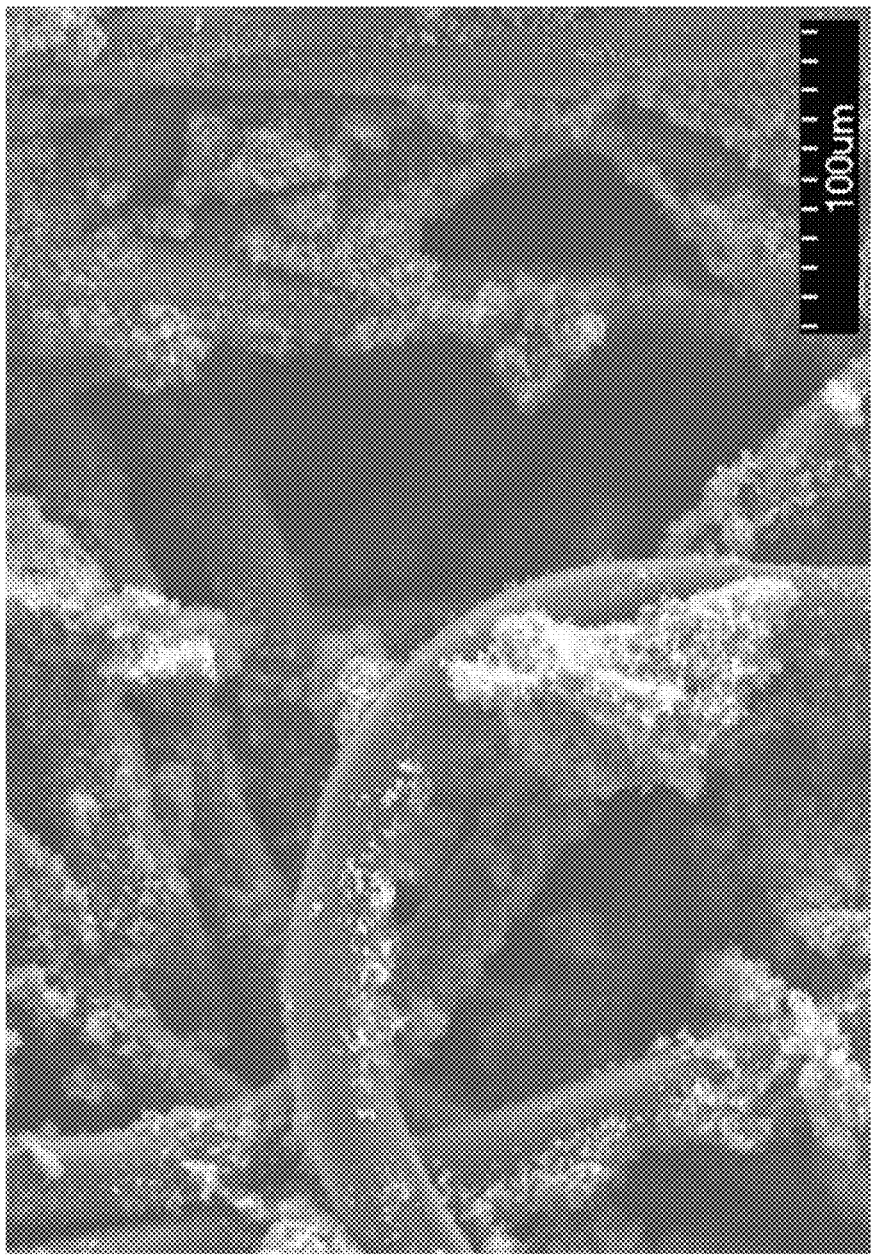
FIG. 4 is a scanning electron microscope image showing fugitive road dust particles aggregated and attached to the fibers of a tortuous-path dust mask.

The secondary filter 160 may be, for example, a household dust mask with a nominal mesh size of about 5 μm. This mask is a tortuous-path fiber filter that is typically used by the public (National Institute for Occupational Safety and Health (NIOSH)-N95) for reducing exposure to dust and other airborne contaminants. This type of filter is advantageous to use because it represents a filtration product typically used by the general population for limiting dust inhalation. Furthermore, it has low loading potential and is effective at grabbing charged particles that are smaller than the filter mesh size. FIG. 4 shows a scanning electron microscope (SEM) image of the secondary filter 160 with fugitive road dust particles smaller than the mesh size attached to the media by Van der Waals forces. Other filters can be used, but loading is a factor that must be considered if a long road distance and large sample quantity are needed. Incorporating smaller pore size filters in the system requires successive layers from larger to smaller pore and mesh sizes. This reduces loading and provides the best analysis of submicrometer particles. The use of commercially available cascading impactors may be an appropriate addition for post-cyclone particle separation if collection plates of the impactors are free from trace element contamination.

Example

An example is described in detail below to illustrate an embodiment of the subsampler described herein. However, it will be understood that the present invention is in no way limited to the example set forth below.

Field Testing

Multiple dust samples were collected at two collection heights (50.8 and 88.9 cm above the road surface). The products of the CFD sampler were characterized using particle size and chemical analysis. The average particle size collected by the cyclone was 17.9 µm, whereas particles collected by the secondary filter were 0.625 µm. No significant difference was observed between the two sample heights tested and duplicates collected at the same height; however, greater sample quantity was achieved at 50.8 cm above the road surface than at 88.9 cm. The cyclone effectively removed 94% of the particles >1 µm, which substantially reduced the loading on the secondary filter used to collect the finer particles; therefore, suction was maintained for longer periods of time, allowing for an average sample collection rate of about 2 g/mi.

The field testing component of this validation effort was done on an unsurfaced gravel/dirt road in rural Ozark County, Mo. (beginning lat. 36.620468, long. −92.26936; ending lat. 36.620511, long. −92.269356). This location was selected because it is extremely rural with minimal vehicular traffic. To minimize variability, all samples were collected in 1 day under identical sampling conditions; other vehicles on this road at the time of sampling would have compromised the results. After a 1-wk period of dry weather in October 2011, nine separate samples were collected on the same 5.63-km segment of the selected road. Five samples were collected with the intake set at 50.8 cm above the road surface and four samples were collected at 88.9 cm above the road surface. The selected sample size was focused on the number of samples that could be collected during a single day. Estimated sample size was calculated using the average number of grams of sample collected per km and substituting this as a population size estimate. Then the equation of Krejcie and Morgan (1970) was used to calculate the sample size of 8 to 10 samples.

The 50.8-cm height was selected to provide a distance from the road surface that would collect a large quantity of sample without collecting coarse material not normally suspended that could be thrown by the tires. Initial testing of the sampler with the intake set directly behind the tires resulted in gravel-size particles being drawn into the suction air stream. This was eliminated by angling the CFD sampler at 45° to avoid tire spray so the sample that is collected represents only particles that were suspend for 10 or more seconds. The 88.9-cm height was selected to represent the average height to the window opening of a compact to a standard size sedan vehicle. This would be the exposure region of suspension for individuals driving unsurfaced roads with their windows down. Wind shear generated along the sides of the moving sampling vehicle can affect sampling efficiency; however, this variability was not quantified. Sample collection times for this analysis ranged from 15 to 17 min, with no stoppages during the collection period. There was no change in static pressure from the beginning to the end of each sample, so it was assumed there was no loss of suction during collection due to filter loading. Therefore, per vacuum design specifications, the sampler processed about 83.5 $m^3$ of dust-laden air. Airflow during sampling would likely change for longer road reaches; therefore, this technique may be improved by adding a more precise flow-metering device linked to a continuous data logger. The cyclone sample container was weighed before and after each sampling period to determine the quantity collected. Samples collected by the cyclone were labeled C1 through C9, and those collected by the secondary filter were labeled F1 through F9.

Two additional samples (DU1 and DU2) were collected from unsurfaced gravel or dirt roads located in forested rural settings of the *Viburnum* Trend mining subdistrict of Missouri's lead (Pb) mining and metals processing region. Soils in the region have been shown to contain persistent Pb contamination, making this an ideal place to test the CFD sampler's ability to collect contaminated dust (Bolter et al., 1975; Bornstein, 1989; Rucker, 2001). Sample DU1 represents an 8-km reach of unsurfaced road (beginning lat. 37.657778, long. −91.178611; ending lat. 37.683333, long. −91.166667) that was traveled twice to accumulate a large quantity of sample. This sample was collected in September 2011, and the weather conditions were extremely dry with an air temperature of 36.7° C. (98° F.). The road surface was primarily composed of quarry stone layers on top of native soil with an overall well maintained appearance. The road terminated at a gated fire-access road that was not passable by the air-sampling vehicle. There was no other traffic on this road during the 30-min sampling period.

Sample DU2 represents a 20.4-km reach of unsurfaced road that follows a ridge top in a heavily forested area (beginning lat. 37.533333, long. −91.050; ending lat. 37.566667, long. −91.133333). The road is maintained by the U.S. Forest Service and is primarily used for logging operations but also receives some traffic from local residents. Quarry stone additions to this road surface were minimal, so the sample primarily represents dust generated from exposed native soils. This sample was collected in October 2011, and the weather was a mild 15.5° C. (60° F.) with a clear sky. There was no other traffic on this road during the 35-min sampling period.

The test samples collected were characterized using particle size analysis (e.g., scanning electron microscopy (SEM) and energy dispersive spectroscopy (EDS)), and qualitative and quantitative chemical analysis (e.g., partial-digestion chemical analysis). The results demonstrate the utility and representativeness of the sampler.

Particle Size Analysis

Particle sizes were determined from images collected using a Hitachi S-4700 SEM. Samples collected by the cyclone were prepared by suspending small aliquots of dust in ethanol and pipetting drops onto SEM stubs covered in double-sided carbon adhesive tape. To reduce any potential particle size bias, additional samples were prepared by dipping stubs covered with the carbon adhesive tape into an aliquot of sample followed by rinsing with compressed air. The ethanol suspension method alone may be preferential to the smaller particles because the larger particles tend to drop out of the solution more quickly. To improve the randomness of the analysis, images from both preparation methods were used. All cyclone samples were sputter coated using a gold-palladium (Au—Pd) target, with a sputter time of 120 s being sufficient to reduce charging effects.

Dust that was collected on the secondary filter was rinsed from the filter into a collection dish using ethanol. To improve image quality and encourage particle separation, the samples were mounted on a silicon wafer that was mounted on a SEM stub with the carbon adhesive. To increase the number of particles per image, some samples were prepared by simply dipping the carbon-taped stub onto the surface of the filter. All filter dust samples were sputter coated for 240 s with Au—Pd.

Imaging conditions for the cyclone-collected samples included a 10 kV accelerating voltage, 11 nA emission current, 12.3 mm working distance, and zero tilt. The lower secondary electron detector within the microscope produced the best quality image with the least amount of charging effect. All images were acquired at 300× magnification. Instrument imaging conditions for the filter-collected samples included a 10 kV accelerating voltage, 9 nA emission current, 12 mm working distance, and zero tilt. The best image quality was obtained at 10,000× magnification. Particle size was measured manually using the ImageJ software (National Institute of Health, version 1.44p) by measuring the longest axis of a given particle (maximum Feret diameter) identified in each of 10 randomly selected horizontal tracks across the image. Cubic particles were measured on an axis diagonal to the corners on a single plane. Between five and eight images were acquired for each sample. A total of 118 images were collected; of these, 100 images were used for particle size analysis. Graphical and inferential statistics were performed using STATA 9 software (StatCorp).

Chemical Analysis

Cyclone-collected particle samples were analyzed for the trace elements Pb, Zn, Co, Ni, Cu, Cd, and As. For each sample and standard reference material, approximately 0.5 g of material was weighed accurately and added to 50-mL, acid-washed disposable digestion vessels and digested using U.S. Environmental Protection Agency method 200.2 (USEPA, 2003). The chosen digestion method was designed to partially digest dry soil and sediment samples for the determination of trace element concentration with the exclusion of metals bound into digestion-resistant silicate minerals. In general, digestion was accomplished by adding 2 mL of diluted $HNO_3$ mixture (500 mL concentrated trace metal-grade $HNO_3$ to 500 mL ASTM Type I water) and 5 mL of diluted HCl mixture (200 mL concentrated trace metal-grade HCl to 400 mL of ASTM Type 1 water) to the digestion vessels containing the samples. The vessels were digested at approximately 95° C. for 45 min. Ribbed polypropylene watch glasses were placed on the open digestion vessel for the duration of the digestion process. After the hot block digestion time, the samples were allowed to cool, the watch glass residue was rinsed into the vessel using ASTM Type 1 water, and the sample volume was brought to 50 mL using the same water. Samples were capped and shaken before allowing to settle for 24 h. Extracts were decanted from the digestion vessels into precleaned, 200-mL polypropylene storage bottles.

Immediately after digestion, samples were analyzed by inductively coupled plasma-mass spectrometry after appropriate dilution. A model Elan DRCe inductively coupled plasma-mass spectrometry instrument (PerkinElmer SCIEX) equipped with a cyclonic spray chamber with a Meinhard nebulizer and platinum cones was used for analysis. The samples were delivered at 1 mL $min^{-1}$ by a peristaltic pump. The RF power was set at 1500 W. Argon flow rates for the plasma and auxiliary gas were 15.0 and 1.2 L $min^{-1}$, respectively. Quantitation was performed using an internal standard method. A multi-element internal standard mixture purchased from PerkinElmer (PerkinElmer SCIEX) was added continuously online. Arsenic as arsenate was detected by DRC mode to eliminate the chloride interference from the HCl addition during digestion. Oxygen was used as the DRC reaction gas.

To ensure good quality data, USEPA-recommended QA/QC methods were followed. Laboratory quality control included measurement of blanks, standards, and duplicates. All digestion vessels, lids, watch glasses, and extract containers were soaked in 5% $HNO_3$ for 24 h, rinsed with trace element-grade deionized water, and allowed to air dry before using. All laboratory consumables were used once and discarded. National Institute of Standards and Testing standard reference materials SRM 2711 Montana II Soils and SRM 2587 Trace Elements in Soil (contains lead from paint) were analyzed in triplicate to assure method recovery and to measure the variability of the analytical process. Instrument calibration was performed at the element concentration of 0.02 to 50 µg $L^{-1}$ linear range. Good linearity ($R^2$=0.9999-1.0) was obtained. Energy Dispersive Spectrums were acquired using the Hitachi S-4700 and EDAX system. These were used to estimate dust particle compositions and to assist with estimating dilutions for the sample digestions before analysis. The EDS analyses are conducted without standards and thus are semi-quantitative.

Results and Discussion

Size distribution analyses for 2,657 particles were performed from cyclone samples C1 through C9. Sample C9 had the fewest measurements with 150 particles measured, and C2 had the most with 450 particles measured. Distribution of particle size is nearly the same for each sample with some variation in outliers as shown in the box plots of FIG. 5. Group 1 (samples C1-C5) represents samples collected at 50.8 cm above the road surface. The quantity of sample collected at this level ranged from 3 to 11 g (average, 7 g), resulting in a collection average of 2 g $mi^{-1}$. Group 2 (samples C6-C9) represents suspended particles collected at 88.9 cm above the road surface. The quantity of these samples ranged from 2 to 4 g (average, 2.7 g), resulting in a collection average of 0.77 g $mi^{-1}$. For group 1, particle sizes ranged from 1.97 to 92.6 µm; for group 2, particle sizes ranged from 3.31 to 96.1 µm. An uneven paired t test of the means suggests there is no significant difference in particle size within and between the two groups. In general, larger particles were found more often in samples collected at a height of 88.9 cm; however, the presence of these particles was not sufficient to alter the median particle size relative to those collected at 50.8 cm. The mean particle sizes for groups 1 and 2 were 17.3 and 18.6 µm, respectively. A paired t test of these means indicates there is no significant difference. Given this, it was determined that the expected average particle size to be collected by the cyclone is 17.9 µm. This effort does show that large particles ranging from 30 to 90 µm can be suspended to heights of 88.9 cm and possibly higher above the road surface. From a human health perspective, these larger particles could be problematic in contaminated areas where suspension would likely be a driving mechanism for ingestion or inhalation, especially if these large particles are associated with a trace metal contaminant such as Pb.

Particle analysis was not performed on samples DU1 and DU2; however, one image was acquired of cyclone-collected DU2 dusts, and 55 particles were measured. Although the results of this count are insufficient in quantity to assure a random sampling, the range of particles is consistent with those observed in FIG. 5. The minimum and maximum particle sizes were 4.0 and 86.1 µm, respectively. Average DU2 particle size was computed at 20 µm (SD, 13.9 µm).

Figure 6B:
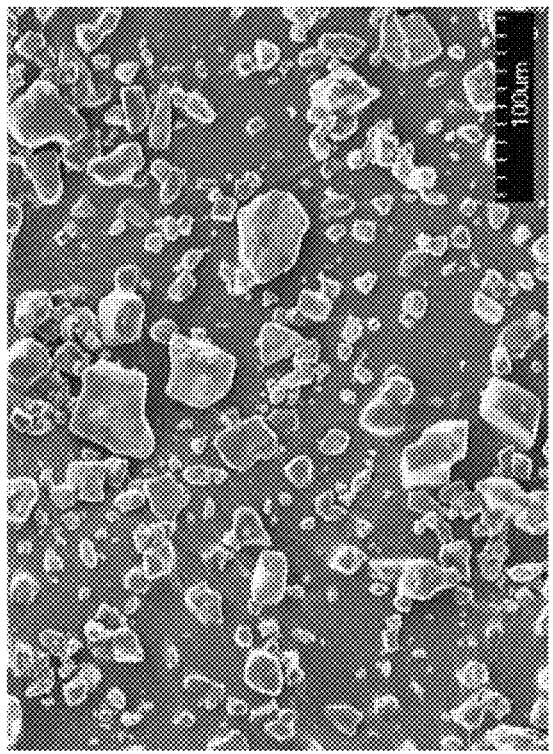
FIG. 6B is a scanning electron microscope image showing particles collected by the cyclone at 88.9 cm above the road surface.
Figure 6A:
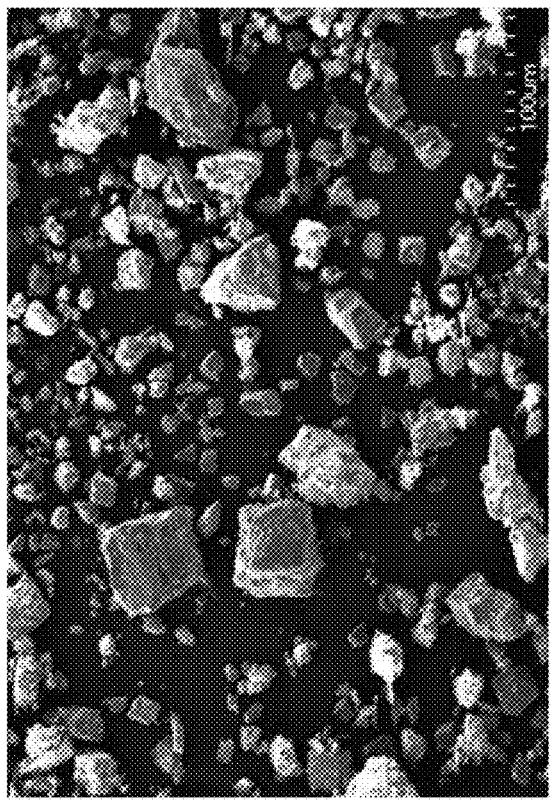
FIG. 6A is a scanning electron microscope image showing particles collected by the cyclone at 50.8 cm above the road surface.

Scanning electron microscopy images show the range of particles size and shape. FIG. 6A shows particles collected by the cyclone at 50.8 cm, and FIG. 6B shows particles collected at 88.9 cm above the road surface. There is no statistically significant difference between the two sample populations. Energy-dispersive spectroscopy mapping combined with phase morphology suggests that most of the particles are quartz, calcite, and Al—Si clays. Ambient soils in the study area are derived primarily from carbonate rock, but most of the particles observed in the imagery are likely from the periodic additions of quarry stone by road maintenance crews. Except for the large difference in scale, the particles in the images do not look that much different from the aggregate on the road surface.

Figure 5:
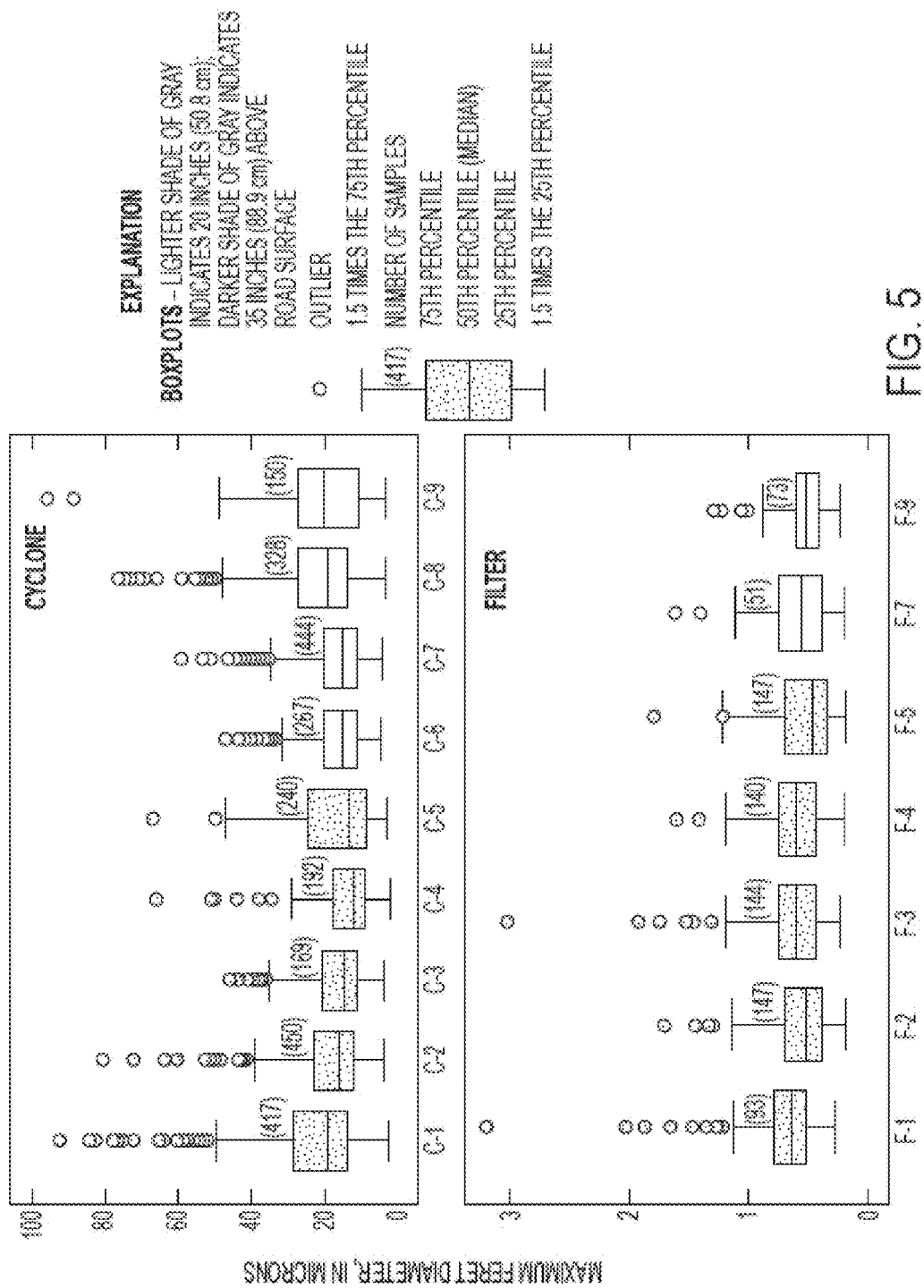
FIG. 5 illustrates box plot data showing the distribution of particle size for cyclone and filter mesh samples of fugitive dust collected above the surface of a gravel/dirt road.

More than 800 particles were measured from images of the mesh filter media for samples F1 through F5, F7, and F9. Particles captured by F1 through F5 ranged from 0.183 to 3.19 µm, and F7 and F9 ranged from 0.187 to 1.63 µm. The distribution of particle size for the seven samples is shown in FIG. 5. In general, there was less variability in the filtered particles than in the cyclone particles, and fewer large outliers were observed. The average particle sizes captured for the filtered samples at 50.8 and 88.9 cm above road surface were 0.625 and 0.561 µm, respectively. A paired t test between all sample means indicates there is no difference. Furthermore, less than 6% of the particles on the filters were larger than 1 µm, indicating that the cyclone efficiently removes about 94% of the larger particles.

Figure 7B:
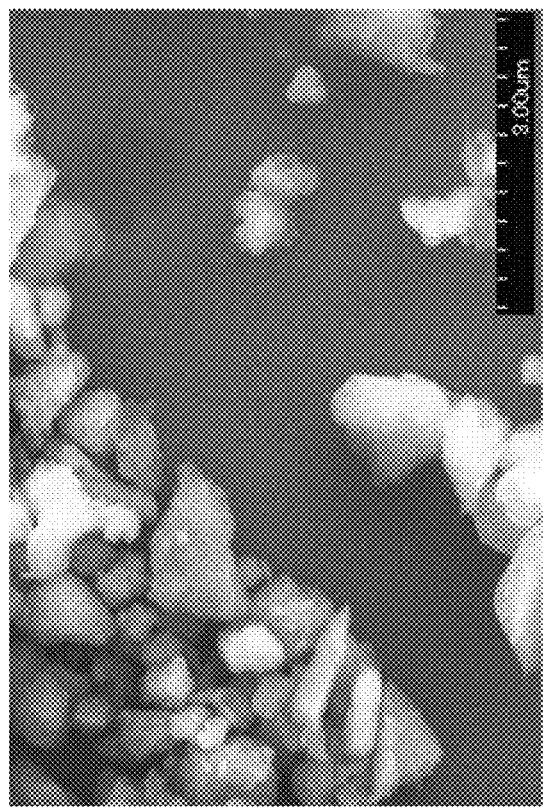
FIG. 7B is a scanning electron microscope image showing filter collected particles magnified 15,300 times.
Figure 7A:
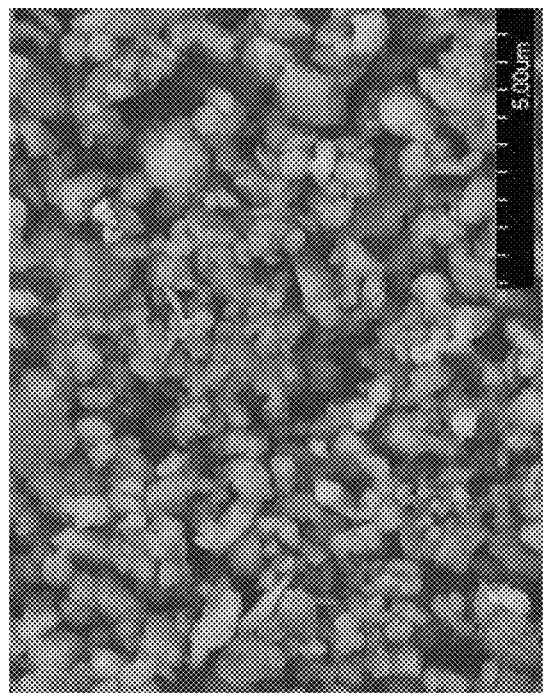
FIG. 7A is a scanning electron microscope image showing filter collected particles magnified 10,000 times.

FIGS. 7A and 7B show the particle distribution from a sample that was prepared by dipping the SEM stub directly onto the collection surface of the filter. FIG. 7A shows filter collected particles magnified 10,000×, and FIG. 7B shows filter collected particles magnified 15,300 times. Particles collected by the dust filter tend to be more rounded and grouped relative to those captured by the cyclone. Energy dispersive spectroscopy was used to provide a semi-quantitative analysis to assist in the determination of particle chemistry and mineralogy. Results suggest that filter-collected particles are primarily quartz, $CaCO_3$, Fe oxide minerals, and Al—Si clays.

Dust samples were further characterized by performing the previously described partial-digestion chemical analysis. Analytical results of samples C1, C2, C3, C5, C7, C8, C9, DU1, DU2, and the standard reference materials are presented in FIG. 8. Samples C4 and C6 were saved to be used as control samples when the CFD sampler is deployed during field studies. Because trace elements are the focus of collection when the sampler is deployed for environmental contamination studies, Pb, Zn, Co, Ni, Cu, Cd, and As were measured. Cyclone-collected samples were singled out for this study because this is where the bulk of sample is collected. Particles in this part of the sampler represent the size ranges that have been shown to be associated with large trace metal concentrations (Wixson et al., 1975).

Variability between samples within the same group height and between samples of different group height was small and within analytical error. A paired t test was performed on groups 1 and 2 for each element and resulted in a determination of no significant difference. The greatest degree of variability between samples was for Pb. Three samples (C1, C2, and C9) fell slightly outside the 95% confidence interval (9.867-13.647) calculated for the mean Pb concentration of the seven samples. Analysis of standard reference materials in triplicate validates the repeatability of the analytical process at larger trace metal concentration—Pb concentration varied less than 0.5% from the mean concentration of the three replicates.

Samples DU1 and DU2 were collected from roadways in regions where Pb contamination has been identified, and it was expected that Pb and Zn concentrations would reflect the concentrations documented by others for soils in the area (Bolter et al., 1975; Bornstein, 1989; Rucker, 2001). The unsurfaced road where sample DU1 was collected is about 4.82 km north of an active secondary recycling smelter and within close proximity to former Pb-ore hauling roads. The road where DU2 was collected also is near the active smelter but to the south and east about 3.22 km. This road was not used for Pb-ore hauling. Background concentration of Pb in Missouri ranges from 20 to 24 mg kg$^{-1}$ (Tidball, 1984). Samples DU1 and DU2 exceeded the background concentration for Pb by 191 and 2.4 times, respectively. It was expected that Pb would be elevated in these samples with respect to the background concentration but not to the degree of variability observed. These results demonstrate the value of the CFD sampler for collecting contaminated dusts. Furthermore, this sampler and the methods tested demonstrate the capability for collecting substantial quantities of fugitive road dusts in Missouri's Pb-producing region. Approximately 15 to 20 g of fugitive dusts were collected from each road surface, with some retention of dust in the air intake tube and on the walls of the cyclone collection container.

Many factors can affect the results of data collection and may show deviations from the results of this analysis. For example, ambient soil moisture and relative humidity at the time of sampling will substantially affect the suspension of dust from a road surface. Therefore, the prevailing weather conditions are an important consideration in planning a field study. Sampling during the dry summer months should provide the best overall outcome, but winter months could be equally productive as long as there is a substantial period of dry weather before sampling.

The type of road material also will affect suspension. During several test runs on various unsurfaced roads throughout Missouri, it was observed that roads with a quarry stone base produced substantially more dust than roads composed solely of the local soil. These roads tended to produce a white suspension that persisted in the atmosphere for more than 10 s and in some cases longer than 1 min. Local soil roads that appear to be predominantly clay, and sand seemed to produce less dust than soil roads mixed with natural stone. The stone component of the road surface mixture tends to support fine particle suspension by increasing surface area friction associated with the moving vehicle tires. Road surfaces composed primarily of local soil produced a brown to reddish suspension. Samples DU1 and DU2 were characteristic of this suspension because both samples are brown to red in color.

Rural unsurfaced roads have reaches that are open to sunlight and covered by forest canopy. During the testing phase of this sampler, it was observed that traveling on shaded reaches of road produced less dust than reaches in full sunlight. Although there has been no quantification of sample volumes surrounding these conditions, it may be appropriate to increase the collection distance where shaded road surfaces predominate. This can usually be accommodated by doubling back on an already sampled reach if a shorter reach is within the study design. Dust suspension also is affected by road surface grading. This activity occurs frequently in rural areas as the road surface becomes rough or in rare cases impassible. Roads that have been recently graded produced the most dust if grading was done after an extended period of dry weather; otherwise, road grading can expose moist layers causing a reduction in dust generation. In many cases, field planning for these conditions can be adjusted by contacting the local county road maintenance office, which generally keeps records on grading dates, quarry stone additions, and general road repairs.

The speed of the collection vehicle also can result in variable quantities of dust collected. The optimal collection speed was determined to be between 40 and 56 km h$^{-1}$ in this study. Traveling speeds less than 40 km h$^{-1}$ generally do not produce suspensions high enough off the road surface, and speeds in excess of 56 km h$^{-1}$ cause shear velocities at the CDF sampler air inlet, causing preferential selection of larger particle sizes. It was observed that local residents using unsurfaced roads on a daily basis generally do not exceed speeds of 64 km h$^{-1}$ because speeds faster than this can be unsafe, damage vehicle finishes, and erode tires. This shows that the optimum sample collection speeds are well aligned with the representative activity in rural areas where these roads predominate.

Wind speed may also be a contributing factor to collection and should be taken into account. High wind speeds likely carry dust away from the CFD sampler before it passes in front of the intake nozzle. Wind speeds should not exceed 16 km h$^{-1}$ on a given sampling day. Exceeding this reduces the quantity of sample collected and may affect a representative collection of particles sizes.

It is not an uncommon occurrence in rural areas for one or more vehicles to be following each other on unsurfaced roads; when this occurs there is substantially more dust put into suspension. In fact, during periods of dry weather exceeding more than a week, a following vehicle on an unsurfaced road may have visibility reduced to 3.05 or 4.57 m, with the dust suspension plume reaching heights exceeding 6.10 m above the road surface. Sample collection during these conditions should increase the sample quantity and provide a more representative sample of fugitive dust exposure to the local population. However, following another vehicle may introduce contamination not specifically associated with dust generated from the road surface. This must be taken into account when interpreting results, and it is suggested that, in areas of expected trace metal contamination where this scenario occurs, a second sampling of the road reach should be performed to confirm results.

The components of the sampler can play a role in the quantity and quality of the sample collected. The filter chosen for this analysis represents one that would be used by the local population to remove airborne contaminants. Filters of progressively smaller mesh size may be used to better quantify submicrometer particle sizes. Also, adding a series of commercially available impactors may help to maintain airflow while capturing submicrometer particles. However, adding smaller mesh-size filters may reduce the airflow through the cyclone, rendering it less efficient.

The development of the CFD sampler provides a new tool with improved capabilities for those conducting fugitive road dust studies worldwide. Under the controlled sampling conditions presented herein, sample collection volume was best at collection heights closer to the road surface; however, both collection scenarios produce a substantial amount of sample in an 8- to 16-km reach of unsurfaced road. Adequate sample volume supports an extensive array of physical and chemical analyses while allowing for the preservation of reference samples for future investigations.

The SEM images, particle size, and chemical analysis performed during this study provide assurance that the CFD sampler 100 produces relatively consistent results. Measurement of more than 3,400 particles from both the cyclone and filters indicates that particle sizes did not differ significantly between samples and sampling heights. Furthermore, chemical analysis for trace elements shows small variability in results. These results provide assurance that the CFD sampler performs under conditions that minimize variability.

The present invention has been described with respect to collecting fugitive dust generated by a moving vehicle. However, with minimal modifications, such as removing or repositioning the air intake conduit 114, this sampler could be used in various moving situations, or in stationary situations where a representative sample is needed to characterize fugitive dust effects at a single location. For example, the air intake conduit 114 can be routed to the inside of a vehicle to quantify the amount of dust suspended inside a moving vehicle. Placing such a configuration inside a school bus that travels on contaminated, unsurfaced roads would provide an assessment of Pb exposure in children. Also, the sampler can be placed on construction vehicles to determine worker exposures and inside factories to monitor worker exposure to airborne manufacturing dusts. In addition, suction unit/vacuum pressures can be adjusted to mimic human respiration, filter pore sizes and materials can be substituted so that they are sufficient for collection of smaller particles that currently pass through the NIOSH-N95 filter, and materials used for the sampler components can be changed to accommodate analysis of organic compounds. In the latter case, the sampler components would be made from either stainless-steel or a Teflon material, or a combination of the two materials.

The subsampler described herein provides several advantages including, but not limited to, the following:

(a) the sampler 100 is easily dismantled and reassembled in the field for replacing parts and cleaning between sampling locations;

(b) the sampler 100 is inexpensive to produce, leading to more dollars going to sample collection and processing as opposed to purchasing equipment;

(c) cyclonic separation allows for longer collection times;

(d) the sampler 100 collects particles in two size ranges: <1 μm and >1 μm;

(e) six to 10 samples can be collected in one day;

(f) the position or height of the air inlet 116 can be easily adjusted; and (g) use of GPS allows tracking of positions of the sampler 100 on specific segments of the road to be sampled.

It will be appreciated by those skilled in the art that modifications and variations of the present invention are possible without departing from the principles and spirit of the invention, the scope of which is defined in the appended claims and their equivalents.

GENERAL BIBLIOGRAPHY ON THE SUBJECT

The following bibliography provides citations to the references cited in the above text. The references are provided merely to clarify the description of the present invention and citation of a reference either in the bibliography below or in the specification above is not an admission that any such reference is "prior art" to the invention described herein.

Barltrop, D., and F. Meek. 1979. Effect of particle size on lead absorption from the gut. Arch. Environ. Health 34:280-285.

Biggins, P., and R. Harrison. 1980. Chemical speciation of lead compounds in street dusts, Environ. Sci. Technol. 14:336-339. doi:10.1021/es60163a005

Bolter, E., T. R. Butz, and J. F. Arseneau. 1975, Mobilization of heavy metals by organic acids in the sons of a lead mining and smelting district, In: Ninth Annual Conference on Trace Substances in Environmental Health, University of Missouri, Columbia, Mo. p. 107-112.

R. E. Bornstein 1989. Long term geochemical effects on lead smelting within the new lead belt, southeast Missouri. M.S. thesis. Univ. of Missouri-Rolla, Rolla, Mo.

Duggan, M. J., and M. J. Inskip. 1985. Childhood exposure to lead in surface dust and soil: A community health problem. Public Health Rev. 13:1-54.

Erel, Y., and J. Torrent. 2010. Contribution of Saharan dust to Mediterranean soil assessed by sequential extraction and Pb and Sr isotopes, Chem. Geol. 275:19-25, doi: 10.1016/j.chemgeo.2010.04.007

Johnson, D. L., and J. K. Bretsch. 2002. Soil lead and children's blood levels in Syracuse, N.Y., USA. Environ. Geochem. Health 24:375-385. doi:10.1023/A: 1020500504167

Kerin, E. J., and H. K. Lin. 2010. Fugitive dust and human exposure to heavy metals around the Red Dog Mine. In: Whitacre, D. M., editor, Reviews of environmental contamination and toxicology, vol. 206. Springer Science+ Business Media, New York. p. 49-63.

Krejcie, R. V., and D. W. Morgan. 1970. Determining sample size for research activities. Educ. Psychol. Meas, 30:607-610.

Murgueytio, A. M., S. A. Clardy, B. N. Shadel, and B. W. Clements. 1998, Relationship between lead mining and blood lead levels children. Arch. Environ. Health 53:414-422. doi:10.1080/00039899809605730

Needleman, H., A. Schell, D. Bellinger, A. Leviton, and E. N. Allred. 1990. The long-term effects of exposure to low doses of lead in childhood; An 11-year follow-up report. N. Engl. J. Med. 322:83-88. doi:10.1056/ NEJM199001113220203

Que Hee, S. S., B. Peace, C. S. Clark, J. R. Boyle, R. C. Bornschein, and P. B. Hammond. 1985. Evolution of efficient methods to sample lead sources, such as house dust and hand dust, in the homes of children. Environ. Res. 38:77-95. doi:10.1016/0013-9351(85)90074-X B. A. Rucker 2001, An investigation of lead and other metal contaminants in soil near the Buick lead recycling smelter, Iron County, Mo. MS thesis, Missouri Univ. of Science & Technology.

Steele, M. J., B. D. Beck, B. L. Murphy, and H. S. Strauss. 1990. Assessing the contribution from lead in mining wastes to blood lead. Regul. Toxicol. Pharmacol. 11:158-190. doi:10.1016/0273-2300(90)90019-8

Thornton, I., D. J. A. Davies, J. M. Watt, and M. J. Quinn. 1990. Lead exposure in young children from dust and soil in the United Kingdom. Environ, Health Perspect. 89:55-60, doi:10.1289/ehp.908955

R. R. Tidball 1984. Geography of soil geochemistry of Missouri agricultural soils. Geochemical Survey of Missouri: U.S. Geological Survey Professional Paper 954-H, 1 U.S. Gov. Print. Office, Washington, D.C. p. 19.

U.S. Environmental Protection Agency. 1983. 435 atmospheric sampling: U.S. Environmental Protection Agency, Air Pollution Training Institute, course manual, chap. 4. http://www.epa.gov/apti/catalog/cc435Manuals.html (accessed 1 Jun. 2012).

U.S. Environmental Protection Agency. 2003. Standard operating procedure for the digestion of aqueous and solid samples using Method 200.2 Hotblock Digestion Technique Method 200.2, Metal Methods 025, Region 5, Chicago, Ill.

Wixson, B. G., E. Bolter, N. L. Gale, D. D. Hemphill, J. C. Jennett, S. R. Koirtyohann, J. O. Pierce, I. H. Lowsley, and W. H. Tranter. 1975. An interdisciplinary investigation of environmental pollution by lead and other heavy metals from industrial development in the new lead belt of southeastern, Missouri: Final report to the National Science Foundation, Research Applied to National Needs, vol. v. I and II. National Science Foundation, Arlington, Va.

Zeneli, L., N. Daci, H. Pacarizi, and M. Daci-Ajvazi. 2011. Impact of environmental pollution on human health of the population which lives nearby Kosovo therrnopower plants. Indoor Built Environ. 20:479-482. doi:10.1177/ 1420326X11409471

What is claimed is:

1. A dust sampling system, comprising: a discrete portable dust sampler, comprising:
    a suction unit to draw in air containing dust particles,
    a cyclone to centrifugally separate the dust particles from the drawn-in air, the cyclone having an air input port, a particle discharge end, and an air output port connected to the suction unit by a suction hose,
    an enclosed dust collection container positioned underneath the cyclone to only receive and store the separated dust particles from the cyclone, and
    an air intake conduit having an air inlet and an air outlet connected to the air input port of the cyclone; and the dust sampler is configured to operate being mounted on an external part of a vehicle on which the dust sampler is placed,
    wherein the suction unit draws in the air containing the dust particles into the air inlet of the air intake conduit while the vehicle moves to collect samples of fugitive dust from a road; whereby the dust collection container is positioned between the suction unit and the air intake conduit;
    a frame on which the dust sampler is mounted, the frame comprising:
    a base having a first end and a second end;
    a suction unit support member having an opening to receive the suction unit, the suction unit support member being attached to the first end of the base at a height sufficient to support the suction unit;
    a conduit support member having a first leg, a second leg, and a conduit arm, the first leg and the second leg being attached to the second end of the base and the conduit arm being attached to top ends of the first leg and second leg and extending out and away from the second end of the base, the conduit support member supporting the air intake conduit and extending over an end of the vehicle;
    a cap mount having an opening to receive the particle discharge end of the cyclone; and a container support member having an opening to receive the dust collection container,
    the container support member being attached to the base between the first leg and the second leg at a height sufficient to support the dust collection container,
    wherein the frame holds the dust collection container, the cyclone, the air intake conduit,
    and the suction unit in place while the vehicle is moving and the samples are being collected.

2. The system of claim 1, further comprising a cap for the dust collection container, the cap being attached to a recess in an underside of the cap mount.

3. The system of claim 1, wherein the suction unit is a shop vacuum having a 5.5 peak horsepower motor and an airflow rate of 5.52 m3/min.

4. The system of claim 1, wherein the suction unit has an air intake port and a filter attached to the air intake port to trap dust particles not deposited in the dust collection container.

5. The system of claim 4, further comprising a static pressure sensor attached to the air intake port to measure airflow changes resulting from filter loading.

6. The system of claim 1, wherein a height of the air inlet of the air intake conduit is adjustable.

7. The system of claim 1, further comprising a Geospatial Position System (GPS) unit with a data logger to track a beginning and ending position of the dust sampler deployed in the moving vehicle.

8. The system of claim 1, further comprising a cascading impactor connected to the suction unit and to the air output port of the cyclone to trap dust particles not deposited in the dust collection container.

9. A cyclonic dust sampler, comprising:
a suction unit to draw in air containing dust particles;
a cyclone that centrifugally separate the dust particles from the drawn-in air, the cyclone having an air input port, a particle discharge end, and an air output port connected to the suction unit by a suction hose with a width narrower than the cyclone;
a discrete enclosed dust collection container positioned underneath the cyclone to only receive and store the separated dust particles from the cyclone; and
an air intake conduit having an air inlet and an air outlet connected to the air input port of the cyclone, a height of the air inlet above a surface to be sampled being adjustable;
a frame on which the dust sampler is mounted, the frame comprising:
a base having a first end and a second end;
a suction unit support member having an opening to receive the suction unit, the suction unit support member being attached to the first end of the base at a height sufficient to support the suction unit;
a conduit support member having a first leg, a second leg, and a conduit arm, the first leg and the second leg being attached to the second end of the base and the conduit arm being attached to top ends of the first leg and second leg and extending out and away from the second end of the base, the conduit support member supporting the air intake conduit and extending over an end of the vehicle;
a cap mount having an opening to receive the particle discharge end of the cyclone; and
a container support member having an opening to receive the dust collection container, the container support member being attached to the base between the first leg and the second leg at a height sufficient to support the dust collection container.

10. The sampler of claim 9, further comprising a cap for the dust collection container, the cap being attached to a recess in an underside of the cap mount.

11. The sampler of claim 9, wherein the suction unit has an air intake port and a filter attached to the air intake port to trap dust particles not deposited in the dust collection container.

12. A method of collecting samples of fugitive dust, comprising: providing a discrete portable dust sampler having:
a suction unit to draw in air containing dust particles,
a cyclone to centrifugally separate the dust particles from the drawn-in air, the cyclone having an air input port, a particle discharge end, and an air output port connected to the suction unit,
an enclosed dust collection container positioned underneath the cyclone to only receive and store the separated dust particles from the cyclone, and
an air intake conduit having an air inlet and an air outlet connected to the air input port of the cyclone;
providing a vehicle and placing the dust sampler on an external part of the vehicle;
positioning a height of the air inlet of the air intake conduit to a desired height above a road surface;
turning on the suction unit to draw air containing the dust particles into the air inlet of the air intake conduit while the vehicle moves to collect samples of fugitive dust from the road;
driving the vehicle along the road for a predefined distance at a predefined speed while tracking a position of the dust sampler as the vehicle moves using a data logger of a Geospatial Positioning System unit; and
removing the dust collection container containing the sample and storing it for subsequent analysis, and before collecting another sampler dismantling the entire dust sampler for washing or replacing with pre-cleaned components of the same specification.

13. The method of claim 12, wherein the vehicle travels at a speed of about 40.2 km/hour to about 56.3 km/hour.

14. The method of claim 12, further comprising attaching a filter to an air intake port of the suction unit to trap dust particles not deposited in the dust collection container.

15. The method of claim 12, further comprising replacing the cyclone and the dust collection container with another pre-cleaned cyclone and another pre-cleaned dust collection container, and collecting additional samples.

16. The method of claim 12, wherein said placing the dust sampler on the vehicle comprises positioning the dust sampler in a pickup truck having a bed, a tailgate, rear tires, and an exhaust pipe so that the air inlet of the air intake conduit reaches over the tailgate behind the rear tires and on an opposite side of the exhaust pipe, and angling the dust sampler at about a 45-degree angle from a longitudinal axis of the tailgate so that the dust sampler collects suspended dust rather than fine sand to granule-sized particles thrown by the rear tires.

17. A dust sampling system,
comprising: a discrete portable dust sampler, comprising:
a suction unit to draw in air containing dust particles,
a cyclone to centrifugally separate the dust particles from the drawn-in air, the cyclone having an air input port, a particle discharge end, and an air output port connected to the suction unit by a suction hose,
an enclosed dust collection container positioned underneath the cyclone to only receive and store the separated dust particles from the cyclone, and
an air intake conduit having an air inlet and an air outlet connected to the air input port of the cyclone; and the dust sampler is configured to operate being mounted on an external part of a vehicle on which the dust sampler is placed,
wherein the suction unit draws in the air containing the dust particles into the air inlet of the air intake conduit while the vehicle moves to collect samples of fugitive dust from a road; whereby the dust collection container is positioned between the suction unit and the air intake conduit; whereby the vehicle includes a bed, a tailgate, rear tires, and an exhaust pipe and the dust sampler is positioned in the truck bed so that the air inlet of the air intake conduit reaches over the tailgate behind the rear tires and on an opposite side of the exhaust pipe, the dust sampler being positioned at a 45-degree angle from a longitudinal axis of the tailgate so that the dust sampler collects suspended dust rather than fine sand to granule-sized particles thrown by the rear tires.

* * * * *